US008445437B2

(12) United States Patent
Shi

(10) Patent No.: US 8,445,437 B2
(45) Date of Patent: May 21, 2013

(54) TREATMENT AND PREVENTION OF CARDIOVASCULAR DISEASE USING MAST CELL STABILIZERS

(75) Inventor: Guo-Ping Shi, Newton, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 159 days.

(21) Appl. No.: 11/878,419

(22) Filed: Jul. 24, 2007

(65) Prior Publication Data

US 2008/0027111 A1 Jan. 31, 2008

Related U.S. Application Data

(60) Provisional application No. 60/833,480, filed on Jul. 27, 2006.

(51) Int. Cl.
*A61K 38/00* (2006.01)
*A61K 31/35* (2006.01)
*A61K 31/12* (2006.01)
*A61P 9/00* (2006.01)
*A01N 43/16* (2006.01)
*A01N 35/00* (2006.01)

(52) U.S. Cl.
USPC ........... 514/16.4; 514/321; 514/456; 514/688

(58) Field of Classification Search
None
See application file for complete search history.

(56) References Cited

U.S. PATENT DOCUMENTS

| | | | |
|---|---|---|---|
| 4,634,699 | A | 1/1987 | McDermed |
| 4,871,865 | A | 10/1989 | Lever |
| 4,923,892 | A | 5/1990 | Lever |
| 5,780,461 | A | 7/1998 | Heath, Jr. et al. |
| 6,207,684 | B1 | 3/2001 | Aberg |
| 6,225,327 | B1* | 5/2001 | Miller et al. ............... 514/342 |
| 6,232,297 | B1* | 5/2001 | Linden et al. ............... 514/46 |
| 6,414,027 | B1* | 7/2002 | Neal ............................ 514/573 |
| 6,777,429 | B1 | 8/2004 | Adam et al. |
| 7,060,827 | B2 | 6/2006 | Singh |
| 7,271,266 | B2 | 9/2007 | Finke et al. |
| 2001/0009917 | A1* | 7/2001 | Gray ............................ 514/310 |
| 2004/0092511 | A1 | 5/2004 | Billstein et al. |
| 2004/0259925 | A1* | 12/2004 | Riedel et al. ............... 514/381 |
| 2004/0259952 | A1 | 12/2004 | Abbas |
| 2005/0182103 | A1 | 8/2005 | Finke et al. |
| 2006/0127511 | A1 | 6/2006 | Tripp et al. |
| 2006/0263350 | A1 | 11/2006 | Lane |
| 2006/0280788 | A1 | 12/2006 | Casey |
| 2007/0244185 | A1* | 10/2007 | Hanko ........................ 514/443 |
| 2009/0093511 | A1 | 4/2009 | Shi |

FOREIGN PATENT DOCUMENTS

WO    WO 2009/045291 A2    4/2009

OTHER PUBLICATIONS

The Merk Manual of Diagnosis and Therapy (online). Whitehouse Station, NJ, USA, Merck & Co. Inc. 2005 (retrieved on Jul. 30, 2007). Retrieved from the Internet. www.merck.com/mmpe/pritn/sec07/ch073/ch073a.html. Coronary Artery Disease, see Etiology and Pathophysiology.*
NIH Heart and Stroke Research: Fact Sheet, American Heart Association, 2004.*
Cardiovascular Disease: Treatment for Stroke, Stanford Hospital & Clinics, 2003.*
The Merck Manual of Diagnosis and Therapy [online]. Whitehouse Station, NJ, USA. Merck & Co., Inc. 2005 [retrieved on Jul. 30, 2007]. Retrieved from the Internet: < http://www.merck.com/mmpe/print/sec07/ch073/ch073a.html>.*
Ward, et al., "Isoform-specific phosphoinositide 3-kinase inhibitors as therapeutic agents," *Current Opinion in Pharmacology* 3:426-434 (2003).
Constantinides, et al., "Mast Cells and Susceptibility to Experimental Atherosclerosis," *Science* 117:505-506 (1953).
Daugherty, et al., "Mouse Models of Abdominal Aortic Aneurysms," *Arterioscler. Thromb. Vasc. Biol.* 24:429-434 (2004).
Daugherty, et al., "Mechanisms of Abdominal Aortic Aneurysm Formation," *Curr. Atheroscler Rep.* 4:222-227 (2002).
Faleiro, et al., "Cerebral Vasopasm: Presence of Mast Cells in Human Cerebral Arteries After Aneurysm Rupture," *Neurosurg.* 54:733-735 (Jun. 1981).
Inoue, et al., "Human Mast Cell Basic Fibroblast Growth Factor in Pulmonary Fibrotic Disorders," *Am. J. Pathol.* 149:2037-2054 (Dec. 1996).
Johnson, et al., "Activation of Matrix-Degrading Metalloproteinases by Mast Cell Proteases in Atherosclerotic Plaques," *Thromb. Vasc. Biol.* 18:1707-1715 (Nov. 1998).
Kovanen, et al., "Infiltrates of Activated Mast Cells at the Site of Coronary Atheromatous Erosion or Rupture in Myocardial Infarction," *Circulation* 92:1084-1088 (1995).
Lätti, et al., "Mast Cell-Mediated Apoptosis of Endothelial Cells in Vitro: A Paracrine Mechanism Involving TNF-α-Mediated Down-Regulation of bcl-2 Expression," *J. Cell. Physiol.* 195:130-138 (2003).
Leskinen, et al., "Mast Cell Chymase Induces Smooth Muscle Cell Apoptosis by a Mechanism Involving Fibronectin Degradation and Disruption of Focal Adhesions," *Arterioscler. Thromb. Vasc. Biol.* 23:238-243 (2003).

(Continued)

*Primary Examiner* — Anna Pagonakis
(74) *Attorney, Agent, or Firm* — Law Office of: Michael A. Sanzo, LLC

(57) ABSTRACT

The present invention is directed to methods of treating or preventing the development of cardiovascular disease by administering compounds that stabilize mast cells. In addition, it includes pharmaceutical compositions which have both a mast cell stabilizer and instructions regarding the use of the stabilizer in treating or preventing cardiovascular disease. The methods and compositions will be of particular value for preventing aneurysms of the abdominal aorta in individuals with atherosclerosis, diabetes, hypertension or a family history of aneurysms.

17 Claims, No Drawings

OTHER PUBLICATIONS

Leskinen, et al., "Regulation of Smooth Muscle Cell Growth, Function and Death in Vitro by Activated Mast Cells: a Potential Mechanism for the Weakening and Rupture of Atherosclerotic Plaques," *Biochem. Pharmacol.* 66:1493-1498 (2003).

Mekori, et al., "Molecular Mechanisms in Allergy and Clinical Immunology," *J. Allergy Clin. Immunol.* 104:517-523 (Sep. 1999).

Mueller, et al., "Measurement of Platelet-Activating Factor in a Canine Model of Coronary Thrombosis and in Endarterectomy Samples from Patients with Advanced Coronary Artery Disease," *Circ. Res.* 77:54-63 (1995).

Pyo, et al., "Targeted Gene Disruption of Matrix Metalloproteinase-9 (Gelatinase B) Suppresses Development of Experimental Abdominal Aortic Aneurysms," *J. Clin. Invest.* 105:1641-1649 (Jun. 2000).

Schwartz, et al., "Structure and Function of the Chemical Mediators of Mast Cells," *Prog. Allergy* 34:271-321 (1984).

Shi et al., "Cathepsin S Required for Normal MHC Class II Peptide Loading and Germinal Center Development," 10:197-206 (Feb. 1999).

Shi, et al., "Deficiency of the Cysteine Protease Cathepsin S Impairs Microvessel Growth," *Circ. Res.* 92:493-500 (Mar. 2003).

Shi, et al., "Cystatin C Deficiency in Human Atherosclerosis and Aortic Aneurysms," *J. Clin. Invest.* 104:1191-1197 (Nov. 1999).

Toda, et al., "Mechanism of Histamine Actions in Human Coronary Arteries," *Circ. Res.* 61:280-286 (Aug. 1987).

Wang, et al., "Cathespsin S Controls Angiogenesis and Tumor Growth via Matrix-Derived Angiogenic Factors," *J. Biol. Chem.* 281:6020-6029 (Mar. 2006).

Zudaire, et al., "Adrenomedullin is a Cross-Talk Molecule that Regulates Tumor and Mast Cell Function During Human Carcinogenesis," *Am. J. Pathol.* 168:280-291 (Jan. 2006).

Bingham, et al., "Mast-Cell Responses in the Development of Asthma," *J. Allergy Clin. Immunol.* 105:S527-S534 (Feb. 2000).

Coussens, et al., "Inflammatory Mast Cells Up-Regulate Angiogenesis During Squamous Epithelial Carcinogenesis," *Genes Dev.* 13:1382-1397 (1999).

Eigen, et al., "Evaluation of the Addition of Cromolyn Sodium to Bronchodilator Maintenance Therapy in the Long-Term Management of Asthma," *J. Allergy Clin. Immunol.* 80(4):612-621.

Galli, et al., "Mast Cells in the Development of Adaptive Immune Responses," *Nat. Immunol.* 6(2):135-142 (Jan. 2005).

Lee, et al., "Mast Cells: A Cellular Link Between Autoantibodies and Inflammatory Arthritis," *Science* 297:1689-1692 (Sep. 2002).

Robbie-Ryan, et al., "The Role of Mast Cells in Allergy and Autoimmunity," *Curr. Opin. Immunol.* 14:728-733 (2002).

Secor, et al., Mast Cells Are Essential for Early Onset and Severe Disease in a Murine Model of Multiple Sclerosis, *J. Exp. Med.* 191:813-822 (Mar. 2000).

Sun, et al., Mast Cells Modulate the Pathogenesis of Elastase-Induced Abdominal Aortic Aneurysms in Mice, *J. Clin. Invest.* 117(11):3359-3368 (Nov. 2007).

Sun, et al., "Mast Cells Promote Atherosclerosis by Releasing Proinflammatory Cytokines," *Nat. Med.* 13(6):719-724 (Jun. 2007).

Wild, et al., "Quantitative Assessment of Angiogenesis and Tumor Vessel Architecture by Computer-Assisted Digital Image Analysis: Effects of VEGF-Toxin Conjugate on Tumor Microvessel Density," *Microvasc. Res.* 59:368-376 (2000).

Wolters, et al., "Tissue-Selective Mast Cell Reconstruction and Differential Lung Gene Expression in Mast Cell-Deficient $Kit^{W-sh}$/$Kit^{W-sh}$ Sash Mice," *Clin. Exp. Allergy* 35:82-88 (Jan. 2005).

Xu, et al., "Proteolytic Exposure of a Site Within Collagen Type IV is Required for Angiogenesis and Tumor Growth in Vivo," *J. Cell Biol.* 154:1069-1079 (2001).

International Preliminary Report on Patentability for PCT/US2007/016622 filed Jul. 25, 2007.

Rao, et al., "Anti-Inflammatory Activity of a Potent, Selective Leukotriene $A_4$ Hydrolase Inhibitor in Comparison with the 5-Lipoxygenase Inhibitor Zileuton," *J. Pharmacol. Exp. Therapeutics* 321:1154-1160 (Mar. 2009).

Cuzzocrea, et al., "5-Lipoxygenase modulates colitis through the regulation of adhesion molecule expression and neutrophil migration," *Lab. Invest.* 85:808-822 (Apr. 2005).

Zouboulis, et al., "Zileuton, an Oral 5-Lipoxygenase Inhibitor, Directly Reduces Sebum Production," *Dermatology* 210:36-38 (Jan. 2005).

Li, et al., "Oxygen-Glucose Deprivation Activates 5-Lipoxygenase Mediated by Oxidative Stress Through the p38 Mitogen-Activated Protein Kinase Pathway in PC12 Cells," *J. Neurosci. Res.* 87:991-1001 (Feb. 2009).

Coffee, et al., "Peroxynitrate-Induced Nitrotyrosination of Proteins is Blocked by Direct 5-Lipoxygenase Inhibitor Zileuton," *J. Pharmacol. Exp. Ther.* 299:198-203 (Apr. 2001).

Clarke et al., "A Comparison of the Efficacy of Ketotifen (HC 20-511) With Sodium Cromoglycate in Skin Test Positive Asthma," *Br. J. Clin. Pharmac.* 10:473-476 (1980).

Geoffrey, et al., "Evidence of a Functional Role for Mast Cells in the Development of Type 1 Diabetes Mellitus in the BioBreeding Rat," *J. Immunol.* 177:7275-7286 (2006).

Brakenhielm, et al., "Angiogenesis in Adipose Tissue," *Methods in Mol. Biol.* 456:65-81 (Jun. 2008).

Cannon, et al., "Brown Adipose Tissue: Function and Physiological Significance," *Physiol. Rev.* 84:277-359 (2004).

Crandall, et al., "A Review of the Microcirculation of Adipose Tissue: Anatomic, Metabolic, and Angiogenic Perspectives," *Microcirculation* 4(2):211-232 (1997).

Duttlinger, et al., "The $W^{sh}$ and *Ph* Mutations Affect the *c-kit* Expression Profile: *c-kit* Misexpression in Embryogenesis Impairs Melanogenesis in $W^{sh}$ and *Ph* Mutant Mice," *Proc. Natl. Acad. Sci. USA* 92:3754-3758 (Apr. 1995).

Fantuzzi, "Adipose Tissue, Adipokines, and Inflammation," *J. Allergy Clin. Immunol.* 115:911-919 (May 2005).

Friedman, et al., "Leptin and the regulation of body weight in mammals," *Nature* 395:763-770 (Oct. 1996).

Kintscher, et al., "T-lymphocyte Infiltration in Visceral Adipose Tissue," *Arterioscler. Thromb. Vasc. Biol.* 28:1304-1310 (2008).

Koban, et al., "Chronic REM-Sleep Deprivation of Rats Elevates Metabolic Rate and Increases UCPI Gene Expression in Brown Adipose Tissue," *Am. J. Physiol. Endocrinol. Metab.* 289:E68-E74 (Jul. 2005).

Liu, et al., "Genetic deficiency and pharmacological stablization of mast cells reduce diet-induced obesity and diabetes in mice," *Nature Medicine* 15(8):940-945 (Aug. 2009), with supplementary figures and tables attached.

Pang, et al., "Macrophage Infiltration into Adipose Tissue May Promote Angiogenesis for Adipose Tissue Remodeling in Obesity," *Am. J. Physiol. Endocrinol. Metab.* 295:E313-E322 (May 2008).

Rocha, et al., "Interferon-γ, a Th1 Cytokine, Regulates Fat Inflammation: A Role for Adaptive Immunity in Obesity," *Circ. Res.* 103:467-476 (Aug. 2008).

Rupnick, et al., "Adipose Tissue Mass can be Regulated Through the Vasculature," *Proc. Natl. Acad. Sci. USA* 99(16):10730-10735 (Aug. 2002).

Shepherd, et al., "Adipose Cell Hyperplasia and Enhanced Glucose Disposal in Transgenic Mice Overexpressing GLUT4 Selectivity in Adipose Tissue," *J. Biol. Chem.* 268(30):22243-22246 (Oct. 1993).

Shi, et al., "Molecular Cloning and Expression of Human Alveolar Macrophage Cathepsin S, an Elastinolytic Cysteine Protease," *J. Biol. Chem.* 267(11):7258-7262 (Apr. 1992).

Skoura, et al., "Essential Role of Sphingosine 1-Phosphate Receptor 2 in Pathological Angiogenesis of the Mouse Retina," *J. Clin. Invest.* 117(9):2506-2516 (Sep. 2007).

Taleb, et al., Cathepsin S Promotes Human Preadipocyte Differentiation: Possible Involvement of Fibronectin Degradation, *Endocrinology* 147(10):4950-4959 (2006).

Weisberg, et al., "Obesity is Associated with Macrophage Accumulation in Adipose Tissue," *J. Clin. Invest.* 112(12):1796-1808 (Dec. 2003).

Wu, et al., "T-Cell Accumulation and Regulated on Activation, Normal T Cell Expressed and Secreted Upregulation in Adipose Tissue in Obesity," *Circulation* 115:1029-1038 (Feb. 2007).

Yang, et al., "Cathepsin L Activity Controls Adipogenesis and Glucose Tolerance," *Nat. Cell Biol.* 9(8):970-977 (Aug. 2007).

Avenell, et al., "What interventions should we add to weight reducing diets in adults with obesity? A systematic review of randomized controlled trails of adding drug therapy, exercise, behaviour therapy or combinations of these interventions," *J. Hum. Nutr. Dietet.* 17(4):293-316 (2004).

International Search Report for PCT/US07/16622 completed on Mar. 27, 2008, mailed on Apr. 17, 2008 and posted on the WIPO website on Jul. 31, 2008.

Written Opinion of the International Searching Authority for PCT/US07/16622, completed on Mar. 31, 2008, mailed on Apr. 17, 2008 and posted on the WIPO website on Jan. 27, 2009.

Database Medline; NLM149739669; XP-002674853; Schwarzer, et al., "Ketotifen alone or as additional medication for long-term control of asthma and wheeze in children." Cochrane Database of Sytematic Reviews (2004).

* cited by examiner

TREATMENT AND PREVENTION OF CARDIOVASCULAR DISEASE USING MAST CELL STABILIZERS

CROSS REFERENCE TO RELATED APPLICATIONS

The present application claims priority to, and the benefit of, U.S. provisional application 60/833,480, filed on Jul. 27, 2007, the contents of which is hereby incorporated by reference in its entirety.

STATEMENT OF GOVERNMENT FUNDING

The United States Government has a paid-up license in this invention and the right in limited circumstances to require the patent owner to license others under reasonable terms as provided for by the terms of NIH grant HL60942, awarded by the Department of Health and Human Services.

FIELD OF THE INVENTION

The present invention is directed to compositions and methods that are useful in the treatment and prevention of cardiovascular diseases, especially aneurysms of the abdominal aorta.

BACKGROUND OF THE INVENTION

Cardiovascular disease, especially atherosclerosis, is the leading cause of death in the United States. One complication often occurring in people with atherosclerosis is the development of abdominal aortic aneurysms (AAA). These aneurysms occur in about 5% of males over the age of 60 and in a lower percentage of females. Risk factors include smoking, a family history of the disease, diabetes and high blood pressure. Atherosclerosis may be treated with medications designed to lower cholesterol levels or blood pressure and with a variety of surgical techniques. Abdominal aneurysms may be treated surgically.

Mast cells (MCs) are recognized as essential effector cells in the elicitation of the allergic response by releasing cytoplasmic granules, whose contents promote allergic inflammation upon sensitization by IgE or complement factors (Schwartz, et al., *Prog. Allergy* 34:271-321 (1984); Mekori, et al., *J. Allergy Clin. Immunol.* 104:517-523 (1999)). Recent biochemical and histological observations suggest that MCs may also participate in blood-borne leukocyte recruitment (Mekori, et al., *J. Allergy Clin. Immunol.* 104:517-523 (1999)), smooth muscle cell (SMC)/endothelial cell (EC) proliferation (Toda, N., *Circ. Res.* 61:280-286 (1987); Inoue, et al., *Am. J. Pathol.* 149:2037-2054 (1996); Mueller, et al., *Circ. Res.* 77:54-63 (1995)), apoptosis (Latti, et al., *J. Cell. Physiol.* 195:130-138 (2003); Leskinen, et al., *Arterioscler. Thromb. Vasc. Biol.* 23:238-2343 (2003); Leskinen, et al., *Biochem. Pharmacol.* 66:1493-1498 (2003)), T-lymphocyte migration and activation (Mekori, et al., *J. Allergy Clin. Immunol.* 104:517-23 (1999)), angiogenesis (Zudaire et al., *Am. J. Pathol.* 168:280-291 (2006)), and matrix remodeling (Daugherty, et al., *Curr. Atheroscler. Rep.* 4:222-227 (2002)).

A role for MCs in vascular wall remodeling was proposed more than half a century ago and accumulation of MCs correlates with human and murine atherogenesis (Constantinides, *Science* 117:505-506 (1953); Kovanen, et al., *Circulation* 92:1084-1088 (1995)). In addition, the appearance of MCs in human cerebral arteries after aneurysm rupture has been reported (Faleiro, et al., *J. Neurosurg.* 54:733-5 (1981)).

If it can be established that MCs are necessary for the development of atherosclerosis or AAA, then methods of treatment and prevention aimed specifically at altering the activity of these cells could be developed. Known methods for the treatment of allergies based upon altering MC function would have the potential of also being useful for cardiovascular disease.

SUMMARY OF THE INVENTION

The present invention is based upon the discovery that mast cells are necessary for the development of atherosclerosis and abdominal aortic aneurysms. Mice lacking mast cells completely fail to develop atherosclerotic plaques or aortic aneurysms under conditions in which wild type mice develop these conditions. It has also been found that aneurysms and atherosclerosis can be prevented in animals if they are treated with agents that stabilize mast cells. Although mast cell stabilizing drugs have been marketed for allergies, they are not currently used for the treatment of cardiovascular disease.

In its first aspect, the invention is directed to a method of treating or preventing cardiovascular disease, particularly vascular aneurysms, stroke and atherosclerosis, in a patient by administering an effective amount of a drug that stabilizes mast cells. The term "effective amount" refers to a sufficient quantity of drug to achieve a therapeutic objective. In the present case, a sufficient amount of mast cell stabilizer should be given to a patient to reduce the risk of an aneurysm or atherosclerotic plaque forming (e.g., by 25, 50 or 75%) or increasing in size. Similarly, an effective amount would constitute a sufficient dosage to reduce the risk of a stroke occurring in patients by 25, 50 or 75%. Typically, between 50 and 1,500 mg of drug will be administered orally to a patient per day. If the drug is delivered nasally, the typical dosage will be between 5-100 mg per day. Preferably, the mast cell stabilizing drug will be divided into two or more equal doses given over a 24 hour period. Preferred drugs are cromolyn, nedocromil, ketotifen and lodoxamide. These may be given in any pharmaceutically acceptable form, including pharmaceutically acceptable salts, such as sodium, disodium, potassium or lithium salts. The most preferred drug is cromolyn sodium or disodium, administered orally at a dosage of 200-1,000 mg per day.

The method described above may be performed to prevent the development of a plaque or aneurysm anywhere within a patient's vascular system but will most preferably be used to prevent aneurysms of the abdominal aorta. It will be especially useful in individuals known to be at increased risk of stroke or aneurysm formation, such as people with diabetes, atherosclerosis, hypertension or a family history of aneurysms. In a particularly preferred embodiment, a patient with atherosclerosis will be administered cromolyn, particularly cromolyn sodium or disodium, at a dose of about 200-1,000 mg daily.

In another aspect, the invention is directed to a therapeutic composition having both a mast cell stabilizer and instructions for administering this stabilizer to a patient to prevent or treat atherosclerosis, stroke or a vascular aneurysm. The stabilizer should be part of a pharmaceutical composition in unit dose form and be packaged in a finished pharmaceutical container. The term "unit dose form" refers to a single drug administration entity, such as a tablet, capsule, or quantity of solution. A "finished pharmaceutical container" refers to any of the different types of packaging typically used for pharmaceuticals such as bottles, vials, blister packs, etc. For the purposes of the present invention, a finished pharmaceutical container will include packaging designed for the nasal administration of drugs, i.e., bottles or vials that contain, and can be used to deliver, a solution or powder as a nasal spray. Similarly, a "unit dose form" will include a solution in which drug is dissolved at a concentration that provides a therapeutic effect when administered to a patient nasally or orally in a fixed amount.

The most preferred mast cell stabilizers for inclusion in the therapeutic compositions are cromolyn, nedocromil, ketotifen and lodoxamide. When these drugs are given orally in the form of a tablet or capsule, a unit dose will typically be between 5 and 1,000 mg and more typically between 10 and 500 mg. An equivalent amount would be in a unit dose form administered as an oral solution. If the drugs are given nasally, then solutions should typically contain a sufficient concentration of drug so that a patient receives between 0.1 and 10 mg per spray.

The instructions that form a part of the therapeutic composition may appear on packaging containing the mast cell stabilizer, on the finished pharmaceutical container or as a separate package insert. The instructions will include the dosage of mast cell stabilizer that should be administered to a patient, e.g., to treat or prevent vascular aneurysms, particularly those of the abdominal aorta. The patients indicated for treatment will typically be those at increased risk of stroke or aneurysm formation such as people with diabetes, atherosclerosis, hypertension or a family history of aneurysms.

The invention also includes methods for determining whether a particular compound will be useful as a treatment or preventative for cardiovascular diseases by assaying the compound for its ability to stabilize mast cells. Any of the stabilization assays that are known in the art, particularly those developed to screen compounds for usefulness in the treatment of allergies, may be used for this purpose.

DETAILED DESCRIPTION OF THE INVENTION

The present invention is based, inter alia, upon experiments demonstrating that mast cells accumulate in human and mouse abdominal aortic aneurysms (AAA) and participate in atherogenesis in a mouse atherosclerosis model. A deficiency of mast cells prevents mice from forming aneurysms as the result of aortic perfusion by elastase. While wild-type (n=11) mice were found to develop AAA, no mast cell (MC) null mice tested (n=9) developed lesions. In the same model, stabilization of MC degranulation with disodium cromoglycate complete blocked AAA formation in wild-type mice, suggesting a direct participation by MCs in this disease. In addition, reconstitution of wild-type MCs, but not interleukin 6 deficient MCs, in MC null mice restored the AAA phenotype, suggesting that MCs contribute to AAA pathogenesis by releasing inflammatory mediators. These results have led to the conclusion that mast cell stabilizers are useful in treating or preventing aneurysms, particularly in people prone to aneurysm formation. With respect to atherosclerosis, results in mice indicate that: a) there is an accumulation of MCs in atherosclerotic lesions; b) a lack of MCs attenuates atherosclerosis; and c) activation of MCs enhances atherosclerosis. The results also indicate that the administration of a mast cell stabilizer such as cromolyn, may be used to reduce atherosclerosis.

A. Mast Cell Stabilizers

Drugs that stabilize mast cells have been studied extensively in connection with the treatment of allergies and several of these drugs are available commercially. The most preferred mast cell stabilizers are cromolyn, nedocromil, ketotifen and lodoxamide and may either be purchased or synthesized using methods well known in the art. In addition, any of the other pharmaceutically acceptable mast cell inhibitors described in the art may be used in the invention. These include compounds disclosed in U.S. Pat. Nos. 6,207,684; 4,634,699; 6,207,684; 4,871,865; 4,923,892; 6,225,327; and 7,060,827. Methods for preparing the compounds are presented in each of the U.S. patents along with information on how the compounds may be purified and the forms in which they may be used. These compounds may be given to patients in any pharmaceutically acceptable form, including any pharmaceutically acceptable salt, with the most preferred drug being either sodium or disodium cromolyn.

B. Making of Pharmaceutical Compositions

Mast cell stabilizing drugs may be incorporated into pharmaceutical compositions in accordance with methods that are standard in the art (see e.g., *Remington's Pharmaceutical Sciences*, Mack Publishing Co., (1990)). Formulations may be designed for delivery by any of the routes commonly used in the art, with preparations designed for oral or nasal delivery being preferred. For oral compositions, e.g. tablets or capsules, the mast cell stabilizing drug should typically be present in an amount of between 1 and 500 mg. In compositions for nasal delivery, stabilizers should typically be present at 0.5 mg/ml-50 mg/ml and more preferably at 1 mg/ml-20 mg/ml. Similar concentration ranges may be used in solutions to be taken orally. Although not preferred, other routes of administration may also be employed.

Mast cell stabilizers may be used in conjunction with any of the vehicles and excipients commonly employed in pharmaceutical preparations including water, salt solutions, alcohols, gum arabic, vegetable oils, benzo-alcohols, polyethylene glycol, gelatin, carbohydrates such as lactose, amylase, or starch; magnesium stearate; talc; salycic acid; paraffin; fatty acid esters; polymers; etc. The pharmaceutical preparations can be sterilized and, if desired, mixed with auxiliary agents such as: dispersants; lubricants; preservatives; stabilizers; wetting agents; emulsifiers; salts for influencing osmotic pressure; buffers; coloring agents; flavoring agents; and/or aromatic substances.

Solutions, particularly solutions for injection, can be prepared using water or physiologically compatible organic solvents such ethanol, 1,2-propylene glycol; polygycols; dimethylsulfoxides; fatty alcohols; triglycerides; partial esters of glycerine; and the like. The preparations can be made using conventional techniques and may include sterile isotonic saline, water, 1,3-butanediol, ethanol, 1,2-propylene glycol, polygycols mixed with water, ringers Ringer's solution etc.

C. Dosage Forms and Routes of Administration

The present invention is compatible with any route of administration including oral, peroral, internal, rectal nasal, lingual, transdermal, vaginal, intravenous, intraarterial, intramuscular, intraperitoneal, intracutaneus and subtaneous routes. Dosage forms that may be used include tablets, capsules, powders, aerosols, suppositories, skin patches, parenterals, sustained release preparations and oral liquids, including suspensions solutions and emulsions. The most preferred routes for administration are oral and nasal. If desired, compositions, particularly compositions for injection, may be freeze-dried and lyophilizates reconstituted before administration. Dosage forms may include mast cell stabilizers as the sole active ingredient or they may include other active agents as well. All dosage forms may be prepared using methods that are standard in the art and that are taught in reference works such as *Remington's Pharmaceutical Sciences* (Osol, A, ed., Mack Publishing Co. (1990)).

D. Treatment Methods

The therapeutic objective of the methods described herein is to either reduce the likelihood of a patient developing a vascular aneurysm or atherosclerotic lesion or to prevent the further growth of an existing aneurysm or lesion. Alternatively, the objective is to reduce the likelihood of a patient experiencing a stroke. When used to prevent disease development, the dose administered will be based upon the results of animal studies, e.g., such as those described herein, and clinical studies performed using methods well known in the art. Mast cell stabilizing drugs are already available for the treatment of other conditions, particularly allergies, and existing dosages may serve as a starting point for evaluating dosages effective in preventing or treating aneurysms. Based upon existing knowledge, it is expected that, using oral delivery methods, a patient will typically receive an oral dose of between 50 and 1500 mg of mast cell stabilizer per day, preferably divided into at least two equal doses. When drug is administered nasally, it is expected that an amount of between 5 and 100 mg of stabilizer will be administered each day, again with this amount being divided into several equal doses.

One patient population selected for administration of pharmaceutical compositions containing the mast cell stabilizers will be people that have, or who are known to be at high risk for developing an aneurysm. The latter includes diabetics, patients with hypertension, patients with a family history of aneurysms and, especially, patients with atherosclerosis. In cases where a patient is being treated for an existing lesion, physicians may want to confirm the effectiveness of the treatment using diagnostic techniques well known in the art, particularly imaging methods. Other patient populations will be those that have or are at high risk for experiencing a stroke or developing atherosclerosis. In all cases, treatment methods and dosages will be selected by the attending physician based upon clinical considerations using methods that are well-known in the art.

E. Packaging of Therapeutic Compositions

As described previously, the pharmaceutical compositions containing mast cell stabilizers may be placed in a finished pharmaceutical container and sold along with instructions to physicians regarding the use of the compositions. In the case of preparations for nasal delivery, the pharmaceutical composition will typically be a solution or powder packaged in a device designed for delivering the composition as a spray. Any of the devices know in the art for delivering drugs in this manner are compatible with the present invention. Depending upon the intended route of delivery, other containers may include bottles, vials, ampoules, blister packs etc.

Instructions concerning the use of pharmaceutical compositions may be included on the container with the pharmaceutical composition or as a package insert. Alternatively, the instructions may be included on a box or other package in which the pharmaceutical composition is sold. In all cases, the instructions will indicate that the pharmaceutical compositions are to be administered for the purpose of preventing or treating: a vascular aneurysm, particularly an aneurysm of the abdominal aorta; atherosclerosis; or stroke. A description of the active ingredient(s) will also be included along with information concerning dosage and how the pharmaceutical composition should be administered. Optionally, instructions may also indicate that the pharmaceutical compositions are to be given to patients having a condition that predisposes them to the development of aneurysms, atherosclerosis or stroke. Conditions predisposing a patient to AAA include diabetes, hypertension, a family history of aneurysms, and, especially, atherosclerosis.

F. Assay Methods

The invention also includes methods for evaluating the potential use of a compound in the treatment or prevention of cardiovascular disease based upon its ability to stabilize mast cells. These assays are well known in the art and have been used in conjunction with the identification of agents useful in treating allergies.

One example of an appropriate assay that may be used is described in U.S. Pat. No. 6,225,327. Briefly, mast cells (about 5,000 per assay tube) are incubated at 37° C. for about 15 minutes with the test compound and then exposed to anti-human IgE (about 10 micrograms/ml). After an additional 15 minutes, reactions are terminated by centrifugation. Supernatants are then collected and analyzed for histamine content, e.g., by radioimmunoassay. A comparison is then made between the amount of histamine present in this sample (the "test sample") and the amount in a control preparation obtained by incubating mast cells and anti-human IgE in the absence of test compound. A reduction in histamine content in the test sample as compared to the control is an indication that the test compound is acting to stabilize the mast cells. The effectiveness of a stabilizer will be reflected by the concentration needed to achieve a given level of inhibition, e.g., a 50% reduction in histamine release.

EXAMPLES

I. Mast Cells in the Development of Abdominal Aortic Aneurysms

Detection of MCs in Human AAA Lesions

To examine the existence of MCs in human AAA, we immunostained human frozen sections of AAA lesions with 1% methylene blue. It was found that MCs were readily detected in human AAA lesions but not in normal vessels, suggesting an involvement of MCs in human AAA.

Murine AAA Model and MC Accumulation in Murine AAA Lesions

Chemically induced murine AAA models, including $CaCl_2$—, angiotensin II-, and elastase-induced lesions, are powerful tools for studying AAA pathogenesis at the molecular level (Daugherty, et al., *Arterioscler. Thromb. Vasc. Biol.* 24:429-34 (2004)). Aorta elastase perfusion in mice, first reported from Thompson's group (Pyo, et al., *J. Clin. Invest.* 105:1641-1649 (2000)), has been demonstrated to be both reproducible and reliable in generating AAA in small animals (rats and mice). Fourteen days after elastase perfusion, all mice (100%) showed an enlarged abdominal aorta with clear and extensive vascular-wall elastolysis (Pyo, et al, *J. Clin. Invest.* 105:1641-1649 (2000)).

Using methylene blue staining of frozen sections from elastase perfusion-induced AAA lesions, we detected MCs in AAA lesions, mainly in the perivascular adventitia. However, either methylene blue or toluidine blue is used to detect primarily degranulated MCs, and these reagents are often affected by tissue fixation (Kuther, et al., *Cell Tissue Res.* 293:111-119 (1998)). Therefore, total MCs in murine AAA lesions may be more than what we observed with methylene blue, but a lack of specific antibodies to murine MCs made it difficult to reveal completely the MC distribution in murine tissues.

To develop murine MC-specific antibodies, we recently expressed mouse mast cell protease-4 (mMCP-4) fusion protein with a His-Tag on the N-terminal end and generated rabbit anti-mouse mMCP-4 polyclonal antibody (Proteintech Group, Chicago, Ill.). Using ear tissue extract from transgenic mice expressing the human papillomaviruses (HPV) 16 early-region genes, including the E6/E7 oncogenes, as a positive control (Coussens, et al., *Genes Dev.* 13:1382-1397 (1999)), we detected a 29-kDa fragment, an expected size for mMCP-4 in an immunoblot analysis. In contrast, this antibody did not detect any signals from other primary cultured mouse aortic SMCs, ECs, or MΦs. As anticipated, bone marrow-derived mast cells (BMMCs), which did not express mMCP-4 (Gurish, et al., *J. Exp. Med* 175:1003-1012 (1992)), also did not show mMCP-4 immunoreactivity.

Using this antibody, we were able to detect accumulation of MCs in mouse AAA lesions but not in normal vessels. mMCP-4-positive MCs were further confirmed with methylene blue staining of tissue sections from the same tissue block, although not parallel slides were used. Most methylene blue-positive cells were also positive for mMCP-4. Similar to human AAA lesions, where we detected many methylene blue-positive MCs but not in normal vessels, methylene blue-positive or mMCP-4-positive MC numbers were also increased during the development of murine AAA after aortic elastase perfusion. Unlike other vascular cells, such as SMCs or MΦs, for which we can quantify their contents with computerized measurement and present the data as a percentage of α-actin-positive (SMC) or Mac-3-positive (MΦs) areas (Sukhova, et al., *J. Clin. Invest.* 111:897-906 (2003); Pan, et al., *Circulation* 109:3149-153 (2004); Sukhova, et al., *Circ. Res.* 96:368-375 (2005)), we detected only a few MCs per aortic section with either methylene blue staining or mMCP-4 polyclonal antibody immunostaining. Therefore, we presented data as total methylene blue-detectable cells (mean±SE) per aortic cross section. While no MCs were seen on day 0 (normal vessels), MCs started to appear in the aorta 7 days post-perfusion. At 14 days post-perfusion, when AAAs were formed, many more MCs were detected. These observations demonstrated the likelihood of MC involvement in murine AAA formation.

$Kit^{Wsh}/Kit^{Wsh}$ Mice are Resistant to Elastase-Induced AAA

The increase in the number of MCs in human and murine AAA suggests either that MCs participate in AAA or simply that they serve as another hallmark of this vascular disorder. We recently tested this possibility by introducing the MC-deficient mice ($Kit^{Wsh}/Kit^{Wsh}$) into the elastase perfusion murine AAA model. Although we detected no differences in the diameters of the abdominal aorta pre- or post-perfusion, all 11 C57/Bl6 mice developed aneurysmal lesions 14 days post-perfusion with increase of aortic diameter >100%. In contrast, of 9 MC-null mice ($Kit^{Wsh}/Kit^{Wsh}$), none had detectable AAA lesions. Histologic analysis (Verhoeff-van Gieson staining) confirmed the presence of better-preserved aortic wall elastic laminae in MC-null mice whereas there was increased elastin fragmentation in the control mice.

MC Stabilization Blocks AAA Formation in C57/BL6 Mice $Kit^{Wsh}/Kit^{Wsh}$ mice fail to develop mature MCs because of an inversion mutation of the c-kit receptor gene (Duttlinger, et al. *Proc. Nat'l Acad. Sci. USA* 92:3754-3758 (1995); Wolters, et al., *Clin. Exp. Allergy* 35:82-88 (2005)). Thus, these mice show: defective c-kit signaling, which is required for leukocyte recruitment, adhesion, and migration (Yuan, et al., *J. Exp. Med.* 186:313-323 (1997); Lukacs, et al., *J. Immunol.* 156:3945-3951 (1996); Sivalenka, et al., *Mol. Cell. Biol.* 24:10277-10288 (2004)); mast cell MMP production (Tanaka, et al., *Blood* 94:2390-2395 (1999)); and endothelial cell survival, migration, and microvessel formation (Heissig, et al., *Thromb. Haemost.* 90:570-576 (2003); Matsui, et al., *J. Biol. Chem.* 279:18600-18607 (2004)), all of which are closely linked to the pathogenesis of AAA. Therefore, impaired AAA in $Kit^{Wsh}/Kit^{Wsh}$ mice may result from defective c-kit signaling, although no direct evidence currently suggests the connection of c-kit signaling with AAA.

To test for this possibility, we injected intraperitoneally (i.p.) disodium cromoglycate (DSCG, 25 mg/kg/day in 0.9% saline, Sigma), a widely used MC stabilizer, into elastase-perfused C57/BL6 mice. Fourteen days post-perfusion, we measured both aortic expansion (aortic diameter, AD) and elastin degradation (Verhoeff-van Gieson staining). None of the mice injected with DSCG developed AAA lesions 14 days post-perfusion, similar to what was seen in $Kit^{Wsh}/Kit^{Wsh}$ mice. Although clear elastin degradation was detected in $C^{57}$/BL6 control mice, both $Kit^{Wsh}/Kit^{Wsh}$ mice and C57/BL6 mice treated with DSCG failed to show comparable elastin degradation, suggesting that impaired AAA in MC-null mice was not due to interruption of c-kit signaling and that AAA development can be managed by regulating MC stability.

MC Reconstitution Recovers AAA Phenotypes in $Kit^{Wsh}/Kit^{Wsh}$ Mice

To further confirm a role for MCs in AAA, we i.v. injected $Kit^{Wsh}/Kit^{Wsh}$ mice, which were resistant to AAA production, with BMMCs derived by in vitro differentiation of bone marrow stem cells from wt mice and IL-6-deficient mice in the presence of IL-3 and serum stem cell factor (Otsu, et al., *J. Exp. Med.* 165:615-27 (1987)). Five weeks after receiving the injections, mice were perfused with aortic elastase. Methylene blue staining of AAA lesions from wt BMMC-reconstituted $Kit^{Wsh}/Kit^{Wsh}$ mice showed methylene blue-positive BMMCs. Similarly, we also detected methylene blue-positive BMMCs in small lesions from IL-6-deficient BMMC-reconstituted $Kit^{Wsh}/Kit^{Wsh}$ mice (although fewer MCs were detected), and methylene blue-positive MCs also were confirmed with immunostaining with mMCP-4 polyclonal antibody. These observations confirm that 1) reconstituted BMMCs do migrate to mouse aortae during AAA progression; and 2) after migration to the aortae, reconstituted BMMCs behave differently from those cultured in vitro. For instance, reconstituted BMMCs became mMCP-4-positive, whereas in vitro BMMCs lack mMCP-4 mRNA (Gurish, et al., *J. Exp. Med.* 175:1003-1012 (1992)) or protein, consistent with a previous report that in vitro IL-3-differentiated BMMCs undergo phenotypic biochemical changes into tissue compartment-specific (aorta, in this case) MCs after adoptive transfer (Otsu, et al., *J. Exp. Med.* 165:615-27 (1987)). Therefore, reconstituted BMMCs must undergo further maturation to play their roles in situ.

Our murine asthma model also supports this hypothesis. Reconstitution with wt BMMCs completely restored pulmonary hyperresponsiveness in mice deficient in MΦ migration inhibitory factor and reconstituted BMMCs are positive for both mMCP-4 and methylene blue. Most interesting, when wt BMMCs, but not IL-6$^{-/-}$ BMMCs, were used for reconstitution, the AAA phenotypes were restored in $Kit^{Wsh}/Kit^{Wsh}$ mice. Comparable aortic expansion and vessel wall elastin fragmentation were observed in BMMC-reconstituted $Kit^{Wsh}/Kit^{Wsh}$ mice. In contrast, when IL-6$^{-/-}$ BMMCs were used for reconstitution, $Kit^{Wsh}/Kit^{Wsh}$ mice still showed a significant reduction in aortic expansion as compared with control mice.

II. Murine Mast Cells and Their Participation in Atherosclerosis

Increased MCs Correlate with Murine Atherosclerotic Lesion Formation

Chymase/tryptase-positive MCs have been shown to appear in human atherosclerotic lesions, with the highest density in the shoulder regions, where they are prone to erosion or rupture (Cornhill, et al., *Monogr. Atheroscler.* 15:13-19 (1990); Kaartinen, et al., *Arterioscler. Thromb.* 14(6):966-972 (1994)). Lack of specific antibodies for murine MCs made it almost impossible to obtain a complete view of MC distribution in murine tissues, although methylene blue or toluidine blue was used to detect only degranulated MCs and was often affected by tissue fixations (Kuther, et al., *Cell Tissue Res.* 293(1):111-119 (1998)). To develop murine MC-specific antibody, we expressed mouse mast cell protease-4 (mMCP-4) fusion protein with a His-Tag on the N-terminal end and generated rabbit anti-mouse mMCP-4 polyclonal antibody (Proteintech Group, Chicago, Ill.). Using ear tissue extract from transgenic mice expressing the human papillomaviruses (HPV) 16 early-region genes, including the E6/E7 oncogenes, as a positive control, we detected the 29-kDa fragment, an expected size for mMCP-4 in an immunoblot analysis. In contrast, this antibody did not detect any signals from other primary cultured mouse aortic SMCs, ECs, or MΦs. As anticipated, BMMCs, which did not express mMCP-4, also did not show mMCP-4 immunoreactivity.

Using mMCP-4 antibody-mediated immunostaining of mouse atherosclerotic lesion sections from LDLr$^{-/-}$ mice fed of an atherogenic diet 26 weeks, we demonstrated the appearance of mMCP-4-positive MCs mostly in the intima but fewer in the adventitia, similar to what has been described in human atherosclerotic lesions (Kovanen, et al. *Circulation* 92(5): 1084-1088 (1995)). In contrast, no positive staining was detected in normal aorta from LDLr$^{-/-}$ mice or in atherosclerotic lesions from LDLr$^{-/-}$/MC-null (Kit$^{Wsh}$/Kit$^{Wsh}$) mice. In addition to revealing MC localization, mMCP-4 staining also allowed us to quantify MC density in aortic lesions, as we routinely quantify mouse lesion MΦ and SMC contents with MAC-3 and α-actin antibodies. Using the same methodology, we immunostained previously collected lesions in one of our prior cohorts (Sukhova, et al., *J. Clin. Invest.* 111(6):897-906 (2003)) with mMCP-4 polyclonal antibody and demonstrated a correlation of the percent of mMCP-4-positive area with lesion development in LDLr$^{-/-}$ mice using Image Pro software. These observations confirmed an accumulation of MCs during mouse atherogenesis similar to that in human atherogenesis and suggested a participation of MCs in the pathogenesis.

Lack of MCs Attenuates Atherosclerosis in LDLr$^{-/-}$ Mice

To examine whether lack of MCs affects atherogenesis in LDLr$^{-/-}$ mice, we crossbred MC-null mice (Kit$^{Wsh}$/Kit$^{Wsh}$, on a homogenous C57/B16 background (Lyon, et al., *Genet. Res.* 39(3):315-22 (1982); Wolters, et al., *Clin. Exp. Allergy* 35(1): 82-88 (2005); Grimbaldeston, et al., *Am. J. Pathol.* 167(3): 835-848 (2005)) with the LDLr$^{-/-}$ mice (also in pure C57/BL6 background, Jackson Laboratory) and generated double-deficient LDLr$^{-/-}$/Kit$^{Wsh}$/Kit$^{Wsh}$ mice. LDLr$^{-/-}$/Kit$^{Wsh}$/Kit$^{Wsh}$ mice are fertile and appear normal in growth and food/water ingestion. Six-week old male LDLr$^{-/-}$/Kit$^{Wsh}$/Kit$^{Wsh}$ mice (n=5) and LDLr$^{-/-}$ mice (n=5) consumed an atherogenic diet for a period of 26 weeks, followed by atherosclerotic lesion characterizations (Sukhova, et al., *J. Clin. Invest.* 111(6):897-906 (2003)). Atheroma lesions were graded as described previously (Sukhova, et al., *J. Clin. Invest.* 111(6):897-906 (2003)). Our data demonstrated that lack of MCs reduced atherogenesis by >50% in lesion grade. While media sizes did not change significantly, intimal sizes were also reduced approximately 50%, suggesting an essential participation of MCs in diet-induced murine atherogenesis. En face preparation of thoracic-abdominal aorta and oil-red O staining demonstrated a clear reduction of lesion area (lipid deposition) on the thoracic-abdominal aortae.

Previous investigations suggested that MCs release mediators such as TNF-α, thus triggering the expression of EC surface adhesion molecules and releasing tryptase to stimulate EC lymphotactic IL-8 secretion or directly releasing lymphotactin and IL-16 to recruit blood-borne leukocytes (Moller, et al., *J. Immunol.* 151(6):3261-3266 (1993); Compton, et al., *J. Immunol.* 161(4):1939-1946 (1998); Rumsaeng, et al., *J. Immunol.* 158(3):1353-1360 (1997)). In our murine atherosclerosis model, the absence of MCs leads to a significant reduction of lesion MΦs (~40% reduction).

MC Activation Enhances Atherosclerosis in LDLr$^{-/-}$ Mice

We hypothesized that reduced atherogenesis in LDLr$^{-/-}$/Kit$^{Wsh}$/Kit$^{Wsh}$ mice can result from the absence of MCs and/or the lack of MC-associated proinflammatory cytokines, chemokines, and proteases. Kit$^{Wsh}$/Kit$^{Wsh}$ mice fail to develop mature MCs because of the inversion mutation of c-kit receptor gene. Thus, these mice show defective c-kit signaling, which is required for leukocyte recruitment, adhesion, and migration; mast cell MMP production; and endothelial cell survival, migration, and microvessel formation, all of which are closely linked to the pathogenesis of atherosclerosis. Therefore, attenuated atherosclerosis in LDLr$^{-/-}$/Kit$^{Wsh}$/Kit$^{Wsh}$ mice may result from defective c-kit signaling, although no direct evidence currently suggests the connection of c-kit signaling with atherogenesis. To test this possibility, we injected intraperitoneally (i.p.) compound 48/80 (4 mg/kg/day in 0.9% saline, Sigma), a widely used MC degranulation reagent, into atherosclerosis-prone LDLr$^{-/-}$ mice fed an atherogenic diet to produce atherosclerosis. C48/80 i.p. injection has been shown to be effective in stimulating MC degranulation and further enhancing the pulmonary hyperresponsiveness in mice (Oldenburg, et al., *J. Pharmacol. Exp. Ther.* 313(1):319-324 (2005)). Although we used only five male mice per group to examine whether we can modulate atherosclerosis by regulating MC activities, our data strongly suggest that MC activation by C48/80 enhanced atherogenesis by almost 30% as compared with that in animals injected with 0.9% saline.

MC Reconstitution Recovers Atherosclerosis in LDLr$^{-/-}$/Kit$^{Wsh}$/Kit$^{Wsh}$ Mice To further confirm a role for MCs in atherosclerosis, we i.v. injected LDLr$^{-/-}$/Kit$^{Wsh}$/Kit$^{Wsh}$ mice, which showed reduced atherosclerosis, with BMMCs derived by in vitro differentiation of bone marrow stem cells from wild-type mice and IL-6-deficient mice in the presence of IL-3 and serum stem cell factor. Five weeks after receiving the injections, mice began consuming an atherogenic diet for 26 weeks. mMCP-4 immunostaining of aortic atherosclerotic lesions from wild-type BMMC-reconstituted LDL$^{-/-}$/Kit$^{Wsh}$/Kit$^{Wsh}$ mice demonstrated mMCP-4-positive BMMCs. Similarly, we also detected mMCP-4-positive BMMCs from lesions of IL-6-deficient BMMC-reconstituted LDL$^{-/-}$/Kit$^{Wsh}$/Kit$^{Wsh}$ mice. These observations confirm: that reconstituted BMMCs do migrate to mouse aortae after initiation of atherosclerosis, although we have not tested whether reconstituted BMMCs can migrate to aortae without atherosclerosis initiation; and that after migration to the aortae, reconstituted BMMCs behave differently from BMMCs cultured in vitro. For instance, reconstituted BMMCs became mMCP-4-positive, whereas in vitro BMMCs lack mMCP-4 mRNA or protein, consistent with a previous report that in vitro IL-3-differentiated BMMCs undergo phenotypic biochemical changes into tissue compartment-specific (aorta, in this case) MCs after adoptive transfer (Otsu, et al., *J. Exp. Med.* 165(3):615-627 (1987)). Therefore, reconstituted BMMCs must undergo further maturation to play their roles in situ. Our murine asthma model supports this hypothesis. Wild-type BMMC reconstitution completely restored pulmonary hyperresponsiveness in MΦ migration inhibitory factor-deficient mice. Most interesting, when wild-type BMMCs but not IL-6$^{-/-}$ BMMCs were used for reconstitution, we were able to restore the atherosclerotic phenotypes in LDL$^{-/-}$/Kit$^{Wsh}$/Kit$^{Wsh}$ mice. Although media areas at the aortic arches did not change significantly, both lesion grade and aortic intima sizes returned to those of LDLr$^{-/-}$ control mice. In contrast, when IL-6$^{-/-}$ BMMCs were used for reconstitution, LDL$^{-/-}$/Kit$^{Wsh}$/Kit$^{Wsh}$ mice still showed significantly reduced atherogenesis, as compared with LDL$^{-/-}$ control mice.

III. Mast Cell Mediators and Their Effects on Neighboring Vascular Cells

Reduced Levels of IL-6 in Kit$^{Wsh}$/Kit$^{Wsh}$ Mice

Active or degranulated MCs exert their effects via secreted inflammatory mediators, which can be used to regulate vascular cell behaviors, including, for example, cell proliferation, apoptosis, angiogenesis, and protease expression. Some of these MC mediators, such as IL-6, may play important roles in AAA, but observational data from the current literature do not identify the culprit.

To determine whether absence of MCs affects the levels of any proinflammatory cytokines in vivo, we measured serum levels of IL-6, probably the best studied MC cytokine, by ELISA (R&D Systems) from AAA mice. While C57/BL6 mice and Kit$^{Wsh}$/Kit$^{Wsh}$ mice before the surgery had nearly undetectable levels of serum IL-6, levels of this cytokine greatly increased 7 or 14 days after aortic elastase perfusion. In contrast, levels of IL-6 in serum from Kit$^{Wsh}$/Kit$^{Wsh}$ mice remained significantly lower than those in the wt control mice (non-parametric Mann-Whitney test). Such reductions in serum IL-6 may contribute to impaired AAA in Kit$^{Wsh}$/Kit$^{Wsh}$ mice and explain why Kit$^{Wsh}$/Kit$^{Wsh}$ mice reconstituted with IL-6-null BMMCs did not develop appreciable AAA lesions unlike those reconstituted with wt BMMCs.

Mast Cells Release Mediators to Regulate Protease Expression by Vascular Cells

Matrix-degrading proteases participate in AAA (Daugherty, et al., *Arterioscler. Thromb. Vasc. Biol.* 24:429-434 (2004)). For example, a deficiency in cysteine protease Cat S or MMP-9 (Pyo, et al., *J. Clin. Invest.* 105:1641-1649 (2000)) significantly attenuates elastase perfusion-induced AAA in mice. MC-derived chymase and tryptase may mediate MMP activation (Saarinen, et al., *J. Biol. Chem.* 269:18134-18140 (1994); Johnson, et al., *Arterioscler. Thromb. Vasc. Biol.* 18:1707-1715 (1998); Kovanen et al., *Heart Vessels Suppl.* 12:125-127 (1997); Gruber, et al., *J. Clin. Invest.* 84:1657-1662 (1989); Lees, et al., *Eur. J. Biochem.* 223:171-177 (1994)), which may indirectly affect the integrity of the vasculature. A recent finding indicated that regulation of the expression and activity of chymase and CPA, two serine proteases responsible for the production of angiotensin II and the degradation of HDL, requires the cysteine protease cathepsins S and C (Henningsson, et al., *Biol. Chem.* 384:1527-1531 (2003)). Although their mRNA levels were unchanged, protein levels and activities increased significantly in Cat S- and Cat C-deficient MCs, indicating an interaction between the cathepsins and MC proteases.

Human body blots demonstrated a selective expression of cysteine protease Cat S in tissues enriched with antigen-presenting cells (APC), e.g., spleen and lymph node, with other tissues, e.g., liver and kidney, expressing much less of this enzyme (Shi, et al., *J. Biol. Chem.* 269:11530-11536 (1994)). Abnormal levels of Cat S in non-APC-rich tissues may indicate a pathologic change, as occurs in tumors (Fernandez, et al., *Int. J. Cancer.* 95:51-55 (2001)) as well as in atherosclerotic and aneurysmal vessels (Sukhova, et al., *J. Clin. Invest.* 102:576-583 (1998); Shi, et al., *J. Clin. Invest.* 104:1191-1197 (1999)). Inhibition or deficiency of Cat S reduced tumor sizes (Joyce, et al., *Cancer Cell.* 5:443-453 (2004); Wang, et al., *J. Biol. Chem.* 281:6020-6029 (2006)) and lessened the development of both atherosclerosis (Sukhova, et al., *J. Clin. Invest.* 111:897-906 (2003)) and abdominal aortic aneurysms. Using [$^{125}$I]-JPM labeling of cysteine protease active sites (Shi, et al., *J. Biol. Chem.* 267:7258-7262 (1992)), we discovered abnormally high levels of active Cat S in MCs from humans and mice. Unlike normal tissues or most mammalian cells, including MΦs, in which Cat B is still the major cysteine protease (Shi, et al., *J. Biol. Chem.* 267:7258-7262 (1992)), Cat S becomes the main cysteine protease in both human and murine BMMCs, suggesting an unrecognized but perhaps important role of this protease in MCs. Given the established role of MCs as APCs and the observation of increased MCs in atheroma (Kovanen, et al., *Circulation.* 92:1084-1088 (1995)) and AAA, MC-derived Cat S may play several roles in MC biology, e.g., matrix degradation and antigen processing and presentation.

One important hypothesis is that MCs interact with neighboring vascular cells and affect their biology by releasing a spectrum of different mediators. Vascular cells are known to release ECM (extracellular matrix)-degrading proteases upon stimulation, directly affecting vascular wall integrity. Therefore, vascular cells may use MC-derived inflammatory mediators to regulate protease expression. For example, a lack of proinflammatory cytokines (e.g., IFN-γ) or chemokines (e.g., MCP-1) can limit AAA or atherosclerosis in mice (Xiong, et al., *J. Immunol.* 172:2607-2612 (2004); Nagano, et al., *J. Clin. Invest.* 100:550-557 (1997); Gu, et al., *Mol. Cell.* 2:275-281 (1998)), likely via reduced protease expression.

To test this hypothesis, we performed experiments by co-culturing primary vascular smooth muscle cells (SMCs) and endothelial cells (ECs) with BMMCs from several mediator-deficient mice, including IL-6$^{-/-}$, TNF-α$^{-/-}$, IFN-γ$^{-/-}$, IL-18$^{-/-}$, and CD40L$^{-/-}$. As described previously (Wolters, et al., *J. Biol. Chem.* 276:18551-18556 (2001)), bone marrow cells were isolated from tibias and fibias and differentiated into BMMCs in the presence of recombinant murine IL-3 (10 ng/ml, expressed in *E. coli*) and stem cell factor (SCF, 0.1 µg/ml, PeproTec) for 4 to 5 weeks. MC purity, as examined by toluidine blue staining, was reported to exceed 95% (Wang, et al., *J. Biol. Chem.* 281:6020-6029 (2006)) and reached almost 100% in our experiments. No progenitor cell contamination was detected by FACS analysis with FITC-conjugated stem cell antigen-1 (Sca-I, Pharmingen). Mouse aortic SMCs and ECs (Shi, et al., *Circ. Res.* 92:493-500 (2003)) were cultured on a six-well plate until confluence, followed by 24 h of starvation. Fresh medium containing 1% FBS and 1×10$^6$ of different cytokine-deficient BMMCs was added to each well. After 24 h of incubation, non-adhesive BMMCs were removed and adhesive SMCs and ECs were washed with 1×PBS 3~4 times. SMCs and ECs were lysed into pH 5.5 lysis buffer containing 1% Triton X-100, 40 mM sodium acetate, and 1 mM EDTA. Cells were lysed on ice for 1 h, and the protein concentrations were determined with a Bio-Rad Protein Dc assay kit. An equal amount of protein (100 µg/sample) from each lysate was incubated with 1 µl of [$^{125}$I]-JPM for 1 h at 37° C., followed by separation on 14% SDS-PAGE. Wild-type BMMCs induced the activity (and possibly expression as well) of cathepsins B, S, K, and L in SMCs, as compared with nontreated SMCs.

In contrast, IL-6$^{-/-}$ and IFN-γ$^{-/-}$ BMMCs showed the least induction of protease, whereas cathepsin activity in SMCs treated with IL-18$^{-/-}$, TNF-α$^{-/-}$, and CD40L$^{-/-}$ BMMCs did not differ from that in SMCs treated with wt BMMCs, indicating that IL-6 and IFN-γ likely are important inducers of expression of cathepsins in SMCs. Cathepsins S, K, and L are the most strongly affected in SMCs, and all three are potent elastases and collageneases highly expressed in SMCs in human AAA lesions (Shi, et al., *J. Clin. Invest.* 104:1191-1197 (1999)). Therefore, it is possible that increased numbers of MCs in adventitia release IL-6 and IFN-γ to trigger the expression of cathepsins S, K, and L in nearby or even remote SMCs via a cytokine diffusion mechanism.

The results for ECs were different from those for SMCs. All tested BMMCs other than TNF-α$^{-/-}$ BMMCs showed a greater or lesser defect in inducing cathepsin expression in ECs. The levels of all four cathepsins diminished when mediator-deficient BMMCs were cultured with ECs. Therefore, regulation of EC cysteine protease expression, which has proved important for EC migration and microvessel formation (Wang, et al., *J. Biol. Chem.* 281:6020-6029 (2006); Shi, et al., *Circ. Res.* 92:493-500 (2003)), may require mediators (IL-6, IL-18, IFN-γ, and CD40L) from MCs. In contrast, MMP activities were less affected by BMMCs in a gelatin gel zymography assay. When 10 μg of protein from each SMC or EC cell lysate was separated onto a gelatin gel (1 mg/ml) followed by overnight incubation in a calcium buffer, Coomassie staining, and destaining, we could not demonstrate considerable differences in MMP-2 and MMP-9 activities from SMCs and ECs treated with different BMMCs, as compared with non-MC-treated or wt BMMC-treated cells. Therefore, ECs may also use MC-derived proinflammatory cytokines for cysteine protease expression, matrix degradation, EC migration and neovascularization, and ultimately the development of AAA lesions.

BMMC-Derived Mediators Affect Vascular Cell Proliferation and T Cell Activation

BMMCs from mice deficient in IL-6, IFN-γ, CD18, and CD40L and from wt control mice were isolated and tested for their effect on the proliferation of mouse aortic SMCs and ECs. Briefly, SMCs or ECs at a series of dilutions were cultured on 96-well plates in the presence of $1\times10^4$ BMMCs from different mice in 1% FBS RPMI. After 24 h of incubation, BMMCs were washed off three to four times with 1×PBS. The number of cells in each well was determined with CellTiter (Promega) with a standard curve of known cell numbers from the same type. Wild-type BMMCs significantly induced SMC proliferation, as compared with SMCs not treated with MCs. In contrast, mediator-deficient BMMCs had different impacts on SMC proliferation. All such impaired proliferation was statistically significant relative to that of cells treated with wt BMMCs.

EC proliferation was also enhanced by wt BMMCs. However, unlike SMCs, only IFN-γ- and IL-18-null BMMCs had a significant impact on proliferation. Other tested cytokines (TNF-α, CD40L, and IL-6) showed no significant effect, although they still reduced EC proliferation.

MCs activate T cells via both released cytokines and antigen presentation. To assess whether lack of certain mediators affected T-cell activation, we isolated CD4$^+$ T cells from balb/c mouse spleens (Shi, et al., *Immunity* 10:197-206 (1999)) and performed an allogeneic mixed lymphocyte reaction (MLR). Briefly, splenocytes from balb/c mice were lysed with red blood cell lysis buffer and further incubated with antibodies to CD8 and I-A$^d$, followed by complement depletion to remove CD8$^+$ T cells and APCs. After two rounds of depletion, CD4$^+$ T cells were added to 96-well plates ($4\times10^5$/well). BMMCs from different mediator-deficient mice (in C57/B16 background) were irradiated and mixed with balb/c CD4$^+$ T cells at different dilutions (400K, 200K, 100K, 50K, 0) as stimulators in RPMI, 10% FBS. After 3 days of co-culture, 1 μCi of [$^3$H]-thymidine was added to each well, followed by another overnight incubation. The cultures were harvested (Tomtec), and incorporated thymidine was assayed in a Betaplate reader (Wallac). Splenocytes from balb/c and C57/B16 mice were used as negative and positive controls for the MLR assay. Wt BMMCs significantly induced CD4$^+$ T cell proliferation/activation with a potency similar to that of C57/B6 splenocytes (positive control). In contrast, lack of IL-6, IFN-γ, and IL-18 in MCs significantly reduced MLR activity. TNF-α$^{-/-}$ and CD40L$^{-/-}$ MCs acted like wt MCs on T-cell activation.

BMMCs Affect Angiogenesis

We performed an angiogenesis assay with mouse aortic rings in matrigels. In a 96-well plate, 1-mm long aortic ring was embedded on top of 50 μl of Matrigel, covered with another 100-150 μl of matrigel, and cultured in 150 μl of RPMI (10% FBS) containing either bFGF (50 ng/ml, positive control) or $1\times10^5$ BMMCs/well from C57/BL6 mice. After 7 days of incubation, microvessel sprouts were measured as area of invasion (mm$^2$) as we described previously (Johnson, et al., *Arterioscler. Thromb. Vasc. Biol.* 18:1707-1715 (1998)). Whereas plain RPMI did not induce angiogenic sprouts from aortic rings, co-incubation of MCs significantly increased the growth of microvessels from the aortic rings, similar to those incubated with bFGF (positive control), providing direct evidence of the effect of MCs on neovascularization.

IV. Mast Cell Stabilization or Activation Directly Affects Atherosclerosis Lesion Formation in LDLr$^{-/-}$ Mice Six weeks old male lipoprotein receptor-deficient (LDLr$^{-/-}$) mice develop atherosclerotic lesions after consuming a Western diet for 12 to 26 weeks. However, the lipoprotein receptor-deficient mice demonstrated >50% reduction of atherosclerotic lesion development at both 12 and 26 weeks under the same dietary conditions when the mice received a daily administration of the mast cell stabilizer disodium cromoglycate (DSCG) (Sigma, 25 mg/kg/day). In contrast, under the same dietary conditions, the lipoprotein receptor-deficient mice showed an increase in atherosclerotic lesions both at 12 weeks and 26 weeks if, instead of DSG, they received a daily injection of the mast cell activator C48/80 (Sigma, 4 mg/kg/day). For these experiments, P<0.05 was considered to be statistically significant (Student t test).

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A method of treating an aneurysm of the abdominal aorta or atherosclerosis in a human subject comprising administering to said subject a pharmaceutical composition in unit dose form comprising an effective amount of cromolyn.

2. The method of claim 1, wherein said method is a method of treating atherosclerosis.

3. The method of claim 1, wherein said method is a method of treating an aneurysm of the abdominal aorta.

4. The method of claim 3, wherein said cromolyn is administered orally at a dose of 50-1500 mg per day.

5. The method of claim 3, wherein said cromolyn is administered nasally at a dose of 5-100 mg per day.

6. The method of claim 3, wherein said cromolyn is cromolyn sodium or cromolyn disodium administered orally at a dose of 200-1000 mg per day.

7. A method of preventing an aneurysm of the abdominal aorta in a human subject having a condition selected from the group consisting of: diabetes; hypertension; a family history of aneurysms; and atherosclerosis, said method comprising administering to said subject a pharmaceutical composition in unit dose form comprising an effective amount of cromolyn.

8. The method of claim 7, wherein said condition is atherosclerosis.

9. The method of claim 2, wherein said cromolyn is administered orally at a dose of 50-1500 mg per day.

10. The method of claim 2, wherein said cromolyn is administered nasally at a dose of 5-100 mg per day.

11. The method of claim 2, wherein said cromolyn is cromolyn sodium or cromolyn disodium administered orally at a dose of 200-1000 mg per day.

12. The method of claim 7, wherein said condition is a family history of aneurysims.

13. The method of claim 7, wherein said condition is diabetes.

14. The method of claim 7, wherein said condition is hypertension.

15. The method of claim 7, wherein said cromolyn is administered orally at a dose of 50-1500 mg per day.

16. The method of claim 7, wherein said cromolyn is administered nasally at a dose of 5-100 mg per day.

17. The method of claim 7, wherein said cromolyn is cromolyn sodium or cromolyn disodium administered orally at a dose of 200-1000 mg per day.

\* \* \* \* \*